(12) United States Patent
Assell et al.

(10) Patent No.: US 8,900,251 B2
(45) Date of Patent: Dec. 2, 2014

(54) RADIAL DEPLOYMENT SURGICAL TOOL

(75) Inventors: Robert Assell, St. Paul, MN (US); Thomas Godfrey Berg, Centerville, MN (US)

(73) Assignee: Zyga Technology, Inc, Minnetonka, MN (US)

( * ) Notice: Subject to any disclaimer, the term of this patent is extended or adjusted under 35 U.S.C. 154(b) by 249 days.

(21) Appl. No.: 12/941,763

(22) Filed: Nov. 8, 2010

(65) Prior Publication Data

US 2011/0295272 A1    Dec. 1, 2011

Related U.S. Application Data

(60) Provisional application No. 61/349,303, filed on May 28, 2010.

(51) Int. Cl.
*A61B 17/22* (2006.01)
*A61B 17/32* (2006.01)
*A46B 7/02* (2006.01)
*A61B 17/16* (2006.01)
*A61B 17/3207* (2006.01)

(52) U.S. Cl.
CPC .......... *A61B 17/32002* (2013.01); *A46B 7/023* (2013.01); *A61B 17/1617* (2013.01); *A61B 17/320725* (2013.01); *A61B 2017/22079* (2013.01); *A61B 2017/320064* (2013.01)
USPC ...................................... 606/127

(58) Field of Classification Search
USPC ............ 604/22; 606/127, 128, 159, 167, 168, 606/170, 171, 172, 180, 200
See application file for complete search history.

(56) References Cited

U.S. PATENT DOCUMENTS

| | | | |
|---|---|---|---|
| 5,242,444 A | | 9/1993 | MacMillan |
| 5,334,205 A | | 8/1994 | Cain |
| 5,551,426 A | * | 9/1996 | Hummel et al. .............. 600/374 |
| 5,800,457 A | * | 9/1998 | Gelbfish ....................... 606/200 |
| 5,827,276 A | * | 10/1998 | LeVeen et al. .................. 606/41 |
| 5,928,239 A | | 7/1999 | Mirza |
| 6,358,251 B1 | | 3/2002 | Mirza |
| 6,440,138 B1 | | 8/2002 | Reiley et al. |
| 6,635,059 B2 | | 10/2003 | Randall et al. |
| 6,679,886 B2 | | 1/2004 | Weikel et al. |
| 6,726,690 B2 | | 4/2004 | Eckman |
| 6,740,090 B1 | * | 5/2004 | Cragg et al. .................... 606/79 |
| 6,746,451 B2 | | 6/2004 | Middleton |
| 6,821,276 B2 | | 11/2004 | Lambrecht |
| 6,923,813 B2 | | 8/2005 | Phillips et al. |
| 6,939,351 B2 | | 9/2005 | Eckman |
| D601,711 S | | 10/2009 | Lin |
| 7,699,849 B2 | | 4/2010 | Eckman |
| 7,867,233 B2 | | 1/2011 | Shaolian et al. |
| 7,879,038 B2 | | 2/2011 | Reiley et al. |

(Continued)

FOREIGN PATENT DOCUMENTS

DE    202009006906    7/2009
EP    0 369 603 A1    5/1990

(Continued)

*Primary Examiner* — Ashley Fishback
(74) *Attorney, Agent, or Firm* — Dicke, Billig & Czaja, PLLC

(57) ABSTRACT

A radial deployment surgical tool having an inner shaft, an outer shaft and a function head. The radial deployment surgical tool is adapted for performing surgical procedures within narrow regions within a patient.

13 Claims, 7 Drawing Sheets

(56) References Cited

U.S. PATENT DOCUMENTS

| | | |
|---|---|---|
| 7,909,827 B2 | 3/2011 | Reiley et al. |
| 7,914,545 B2 | 3/2011 | Ek |
| 8,109,957 B2 | 2/2012 | Stad et al. |
| 8,114,084 B2 | 2/2012 | Betts |
| 8,348,950 B2 | 1/2013 | Assell et al. |
| 2001/0000799 A1* | 5/2001 | Wessman et al. ............ 606/200 |
| 2001/0049527 A1 | 12/2001 | Cragg |
| 2003/0191474 A1 | 10/2003 | Cragg et al. |
| 2004/0267269 A1 | 12/2004 | Middleton et al. |
| 2005/0137600 A1* | 6/2005 | Jacobs et al. ............ 606/79 |
| 2005/0159746 A1 | 7/2005 | Grob |
| 2005/0267482 A1 | 12/2005 | Hyde, Jr. |
| 2006/0111780 A1 | 5/2006 | Petersen |
| 2006/0155289 A1 | 7/2006 | Windhager et al. |
| 2007/0123889 A1 | 5/2007 | Malandain et al. |
| 2007/0198020 A1 | 8/2007 | Reiley et al. |
| 2007/0260270 A1 | 11/2007 | Assell |
| 2008/0009861 A1 | 1/2008 | Stark |
| 2008/0009875 A1 | 1/2008 | Sankaran |
| 2008/0091199 A1 | 4/2008 | Cragg |
| 2008/0114364 A1 | 5/2008 | Goldin et al. |
| 2008/0269754 A1 | 10/2008 | Lutz |
| 2008/0294167 A1 | 11/2008 | Schumacher et al. |
| 2009/0138053 A1 | 5/2009 | Assell |
| 2009/0216238 A1 | 8/2009 | Stark |
| 2009/0259261 A1 | 10/2009 | Reiley |
| 2009/0319043 A1 | 12/2009 | McDevitt et al. |
| 2010/0030216 A1 | 2/2010 | Arcenio |
| 2010/0131011 A1 | 5/2010 | Stark |
| 2010/0241123 A1 | 9/2010 | Middleton et al. |
| 2011/0028978 A1 | 2/2011 | Li et al. |
| 2011/0087294 A1 | 4/2011 | Reiley |
| 2011/0098709 A1 | 4/2011 | Malandain et al. |
| 2011/0118796 A1 | 5/2011 | Reiley |
| 2011/0264229 A1 | 10/2011 | Donner |
| 2012/0323285 A1 | 12/2012 | Assell et al. |
| 2013/0030456 A1 | 1/2013 | Assell et al. |

FOREIGN PATENT DOCUMENTS

| | | |
|---|---|---|
| WO | 0234147 | 5/2002 |
| WO | 2005/039651 A2 | 5/2005 |
| WO | 2007016684 A2 | 2/2007 |
| WO | 2007/142830 A1 | 12/2007 |
| WO | 2008/021656 C2 | 2/2008 |
| WO | 2008060277 A2 | 5/2008 |
| WO | 2008103839 A2 | 8/2008 |
| WO | 2009029074 A1 | 3/2009 |
| WO | 2009143496 | 11/2009 |
| WO | 2010017631 A9 | 2/2010 |
| WO | 2010065015 A1 | 6/2010 |
| WO | 2012015976 A1 | 2/2012 |

* cited by examiner

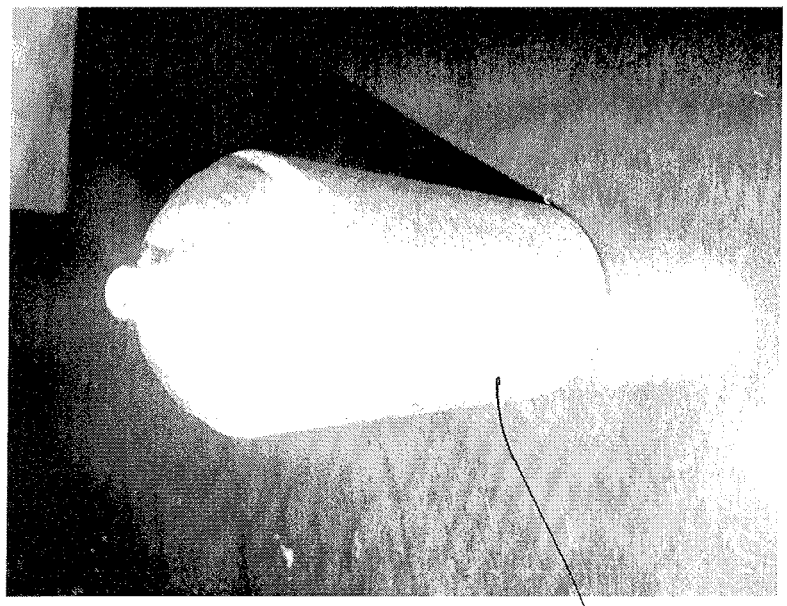
Fig. 6    82
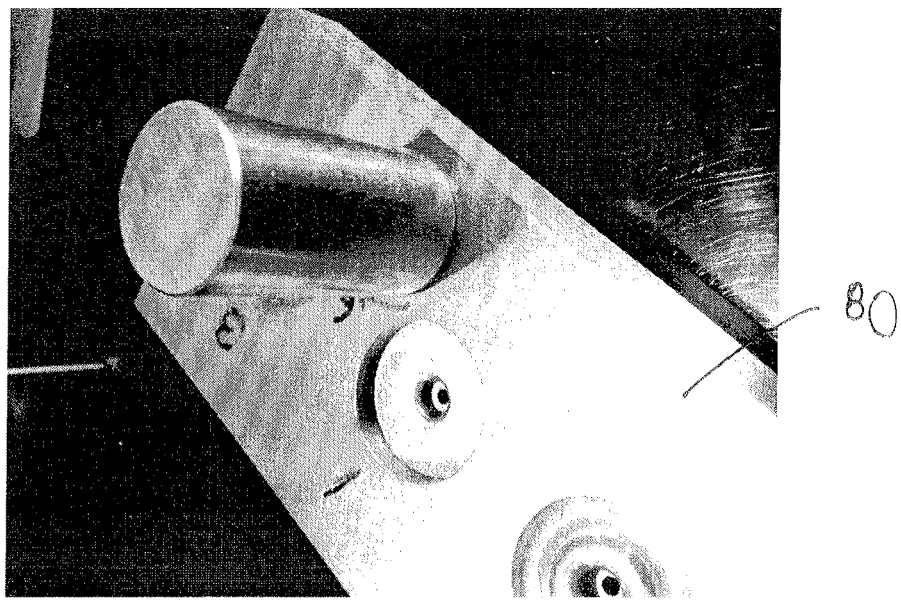
Fig. 7

RADIAL DEPLOYMENT SURGICAL TOOL

REFERENCE TO RELATED APPLICATION

This application claims priority to U.S. Provisional Application No. 61/349,303, which was filed on May 28, 2010, the contents of which are incorporated herein by reference.

FIELD OF THE INVENTION

An embodiment of the invention is directed to a surgical tool. More particularly, the invention relates to a radial deployment surgical tool that is adapted for performing surgical procedures within narrow regions within a patient.

BACKGROUND OF THE INVENTION

While it is generally desirable to perform surgical procedures where the surgeon can directly see the area where the surgical procedure is being performed, this procedure is generally only suitable for surgical procedures that are close to a person's skin because providing an opening that is sufficiently large to view a surgical location that is located deeper within the person's body could require cutting of additional tissue and other components within the person's body. Such additional cutting raises the potential of the patient experiencing a longer recovery time as well as being subjected to an increased likelihood of complications from the surgery.

It has been found that the outcome of the surgery can be enhanced by minimizing the cutting of the patient's tissue during the surgical procedure. One such surgical technique that has been developed to reduce the size of incisions formed in the patient is laparoscopy. While this technique is suitable for use in many applications, laparoscopy is subject to limitations that preclude its use in certain situations.

There are many joints in a person's body where two surfaces move with respect to each other. Over time, certain persons may experience problems caused by the degradation of the adjacent bones or the tissue that is located between the bones. If untreated, these problems could cause significant pain in the patient, which may limit the patient's ability to perform physical activities that require the use of that joint.

Two surgical techniques may be used to treat these joint problems. These surgical techniques are placing an implant between the bones and fusing the bones together. The most appropriate technique may depend on a variety of factors. Regardless of which technique is used, it is desirable to minimize the size of the incision that is used to provide access to the area where the surgical technique is being performed. However, the incision must be large enough to enable the surgeon to prepare the bone surfaces and then to insert the implant and/or fixation devices that are used in conjunction with the surgical technique.

While it may be possible for the surgeon to move the bone surfaces apart from each other when preparing the bone surfaces and inserting the implant and/or fixation device, it is generally desirable to minimize such movement to reduce the potential of damage to the ligaments and/or tendons that surround the joint to reduce the potential of complications and reduce the patient's recovery time.

Certain surgical procedures generate debris that must be removed from the body as part of the surgical procedure. When the surgical procedure includes forming a relatively large incision in the patient, the surgical debris may be removed using a variety of techniques. For example, a suction may be used to remove the surgical debris from the area where the surgical procedure was done.

Additionally, when it is possible to perform the surgical procedure through a relatively large incision in the patient, the surgical debris may be left in relatively large pieces to facilitate removing the surgical debris from the patient. These pieces may be grasped to remove them from the area where the surgical procedure is being performed.

On the other hand, certain surgical procedures are performed in regions of the patient that do not permit forming a relatively large incision or otherwise has restricted access. One such area with limited access and visibility is encountered when cartilage between the sacrum and the ilium is cut up to facilitate removal in preparation for fusion of the sacroiliac joint. Another area with limited access and visibility is encountered when removing an intervertebral nucleus.

SUMMARY OF THE INVENTION

An embodiment of the invention is directed to a radial deployment surgical tool. The radial deployment surgical tool is adapted for performing surgical procedures within narrow regions within a patient.

A radial deployment surgical tool has an outer shaft, an inner shaft and a functional head. The outer shaft has a distal end and a proximal end. The inner shaft has a distal end and a proximal end. The inner shaft is operably mounted with respect to the outer shaft so that the inner shaft is positioned at least partially in the outer shaft.

The functional head is operably attached to the distal end of the inner shaft. The functional head is movable between a retracted position substantially within the outer shaft to an extended position where at least a portion of the functional head extends outside of the outer shaft.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 6 is a bottom perspective view of a punch for use in shaping the cleaning head.

FIG. 7 is a top perspective view of the punch positioned adjacent the die.

DETAILED DESCRIPTION OF THE PREFERRED EMBODIMENTS

Figure 1:
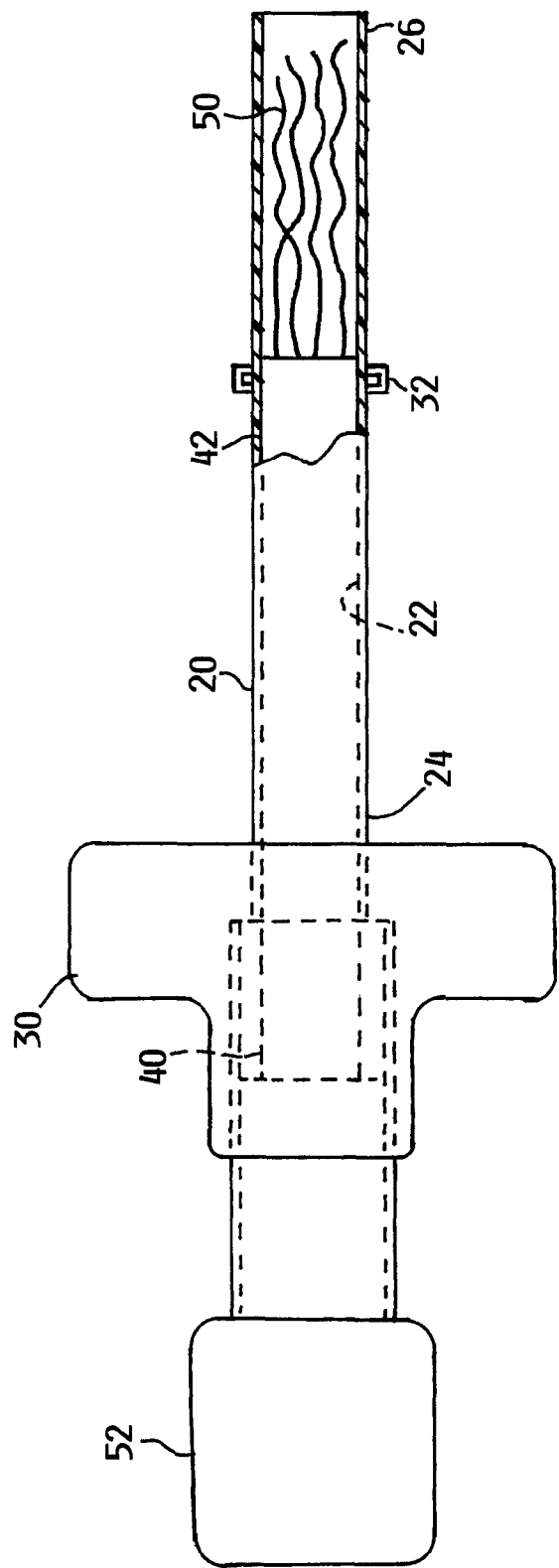
FIG. 1 is a sectional view of a radial deployment surgical tool in a retracted position.

An embodiment of the invention is directed to a radial deployment surgical tool. The radial deployment surgical tool enables surgical procedures to be performed in relatively narrow spaces. As used herein, the term relatively narrow means spaces having a width of less than about ½ of an inch. In certain embodiments, the width of the space is less than about ⅛ of an inch.

The radial deployment surgical tool may be used in a variety of surgical settings. To facilitate using the radial deployment surgical tool in the variety of surgical settings, the radial deployment surgical tool may include a functional head attached to a distal end thereof.

One such suitable surgical setting is forming an opening between two bones that are located proximate each other. In an example of one such suitable surgical procedure is a minimally invasive orthopedic procedure. In this configuration, the functional head may be a cutting head that is attached to a distal end of the radial deployment surgical tool.

In other embodiment, the radial deployment surgical tool may be used for removing materials from between two adjacent bones. This material may have been previously cut or otherwise transformed into relatively small pieces to facilitate removal using the radial deployment surgical tool. A person of skill in the art will appreciate that different devices may be attached to the radial deployment surgical tool depending on the intended use of the radial deployment surgical tool.

An embodiment of the surgical debris removal system, as illustrated at 10 in the figures appended hereto. The surgical debris removal system 10 may be used for removing surgical debris that is generated in conjunction with performing certain surgical techniques within a human body. For example, surgical debris is created when the cartilage between the sacrum and ilium is removed and the surfaces of the sacrum and the ilium are prepared for fusion of the sacroiliac joint.

The surgical debris needs to be removed from between the sacrum and the ilium to facilitate bone growth between the sacrum and the ilium to produce fusion of the sacroiliac joint. Because of the relatively small distance between the sacrum and the ilium and the location of the sacroiliac joint within the human body, there may be challenges in removing the surgical debris.

A person of skill in the art will appreciate that it is possible to use the surgical debris removal system in conjunction with performing other surgical techniques performed in locations having obstructed access that prevents the use of more direct techniques to remove the surgical debris. A non-limiting example of an application in which the surgical debris removal system may be used is removing an intervertebral nucleus.

The surgical debris removal system 10 may generally include an inner shaft 20 that is operably mounted with respect to an outer shaft 22. The outer shaft 22 has a proximal end 24 and a distal end 26. In certain embodiments, the outer shaft 22 is formed with a length that is sufficiently long to facilitate the proximal end 24 to be positioned outside of a patient while the distal end 26 is positioned within the patient proximate to where the surgical debris is to be removed. In certain embodiments, the outer shaft 22 has a length of between about 5 and 30 centimeters.

The outer shaft 22 is formed with a length that enables the outer shaft 22 to be extended through an opening that provides access to the region in which the surgical debris is located. In certain embodiments, the opening can be substantially cylindrical. For example, the opening may have been formed using a drill.

To minimize the trauma to the patient and thereby reduce the patient's recovery time after the surgical procedure is completed, it is generally desired to form the opening to be as small as possible. In certain embodiments, the opening has a diameter of less than about 1 centimeter. In other embodiments, the opening has a diameter of between about 5 and 10 millimeters.

While in certain embodiments the outer shaft 22 is substantially rigid, it is also possible for the outer shaft 22 to be bendable. In embodiments where the outer shaft 22 is bendable, the outer shaft 22 may retain the shape after being bent. Alternatively, the outer shaft 22 may return to the initial shape such as where the outer shaft 22 is substantially straight.

The outer shaft 22 has a central aperture extending therethrough that is adapted to receive the inner shaft 20, as is discussed in more detail below. Proximate the proximal end 24, the outer shaft 22 may have a first gripping mechanism 30 extending therefrom. The first gripping mechanism 30 enhances the ability of a person using the surgical debris removal system 10 to maintain the outer shaft 22 in a desired configuration. The first gripping mechanism 30 may take a variety of configurations. For example, the first gripping mechanism 30 may be substantially cylindrical with a diameter that is greater than a diameter of the outer shaft 22.

Intermediate the proximal end 24 and the distal end 26, a stop mechanism 32 may be provided on an outer surface of the outer shaft 22. The stop mechanism 32 limits a distance in which the outer shaft 22 may be inserted into the opening in the patient.

In certain embodiments, where a cannula is inserted into the opening in the patient, the stop mechanism 32 may engage the cannula to limit a distance at which the outer shaft 22 may be inserted into the patient.

The inner shaft 20 has a proximal end 40 and a distal end 42. The inner shaft 20 may be formed with a length that is greater than a length of the outer shaft 22 such that the proximal end 40 of the inner shaft 20 extends beyond the proximal end 24 of the outer shaft 22 when the distal end 42 of the inner shaft 20 extends beyond the distal end 26 of the outer shaft 22.

This configuration enables a cleaning head 50 that is operably attached to the distal end 42 of the inner shaft 20 to be extended beyond the distal end 26 of the outer shaft 22 to be moved using the proximal end 40 of the inner shaft 20 for collecting surgical debris, as is described in more detail below.

A second gripping mechanism 52 may be attached to the proximal end 40 of the inner shaft 20 to enhance the ability of a person to control the movement of the cleaning head 50. The second gripping mechanism 52 facilitates the person using the surgical debris removal system 10 rotating the inner shaft 20 during the debris collection process.

The second gripping mechanism 52 may have a variety of configurations using the concepts of the invention. For example, the second gripping mechanism 52 may be substantially cylindrical with a diameter that is greater than a diameter of the inner shaft 20.

The cleaning head 50 may include a cleaning head hub 60 from which a plurality of cleaning head arms 62 extend. The hub 60 may have a generally circular shape with an aperture 64 formed therein to facilitate attaching the cleaning head 50 to the inner shaft 20. One technique that may be used to attach the cleaning head 50 to the inner shaft 20 is a screw (not shown).

In certain embodiments, the cleaning head 50 may be removably attached to the inner shaft 22 so that the cleaning head 50 may be detached from the inner shaft 20 such as when the cleaning head 50 needs to be replaced or when it is desired to use a cleaning head 50 having a different configuration in conjunction with the surgical debris removal system 10.

In certain embodiments, one cleaning head 50 is attached to the inner shaft 20. In other embodiments, a plurality of cleaning heads 50 may be attached to the inner shaft 20. The plurality of cleaning heads 50 may each be formed with a similar shape or may be formed with different shapes. Additionally or alternatively, the cleaning heads 50 may be mounted in different orientations to enhance the ability to the cleaning head 50 to latch on to debris.

The cleaning head arms 62 may have a variety of configurations. An important criterion in shaping the cleaning head arms 62 is that an end of the cleaning head arms 62 opposite the cleaning head hub 60 is curved to facilitate surgical debris being snagged by the cleaning head arms 62. Two suitable configurations for the cleaning head arms 62 are set forth in FIGS. 3 and 4.

Figure 3:
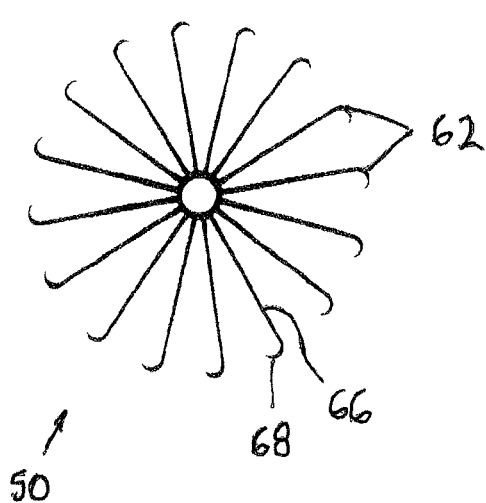
FIG. 3 is a top view of a cleaning head for use with the radial deployment surgical tool where the cleaning head is in a substantially flat configuration.

Ends of the cleaning head arms 62 illustrated in FIG. 3 are curved so that an angle between a main arm portion 66 of the cleaning head arms 62 and the tip portion 68 of the cleaning head arms 62 is an acute angle that is less than about 90 degrees forming a hook-like feature.

The tip portions 68 of the cleaning head arms 62 may also be tapered to a point. The cleaning head arms 62 in FIG. 4 are curved so that an angle between a main arm portion 66 of the cleaning head arms 62 and the end potion 70 of the cleaning head arm 62 is an obtuse angle that is greater than 90 degrees, but generally less than 180 degrees.

Figure 4:
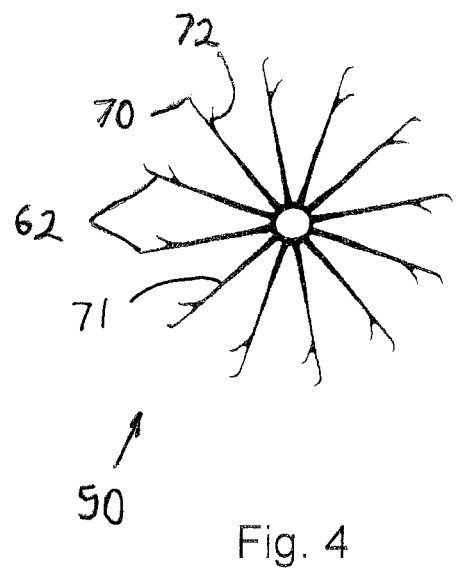
FIG. 4 is a top view of an alternative configuration of the cleaning head where the cleaning head is in a substantially flat configuration.

The cleaning head arms 62 illustrated in FIG. 4 each include a main arm portion 71 and at least two pointed tip portions 70, 72. The tip portions 70, 72 are oriented at an acute angle with respect to the main arm portion 71 from which the tip portions 70, 72 extend. One of the pointed tips 70 is located proximate an end of the cleaning head arm 62 and the other pointed tip 72 is located at an intermediate location on the cleaning head arm 62. While the tips 70, 72 are illustrated as both being oriented in the same direction, it is possible that the tips 70, 72 can be oriented in different directions.

The different directions may be generally oriented in the same plane as the other portions of the cleaning head arm 62. Alternatively or additionally, the tips 70, 72 may be oriented in directions that are not generally aligned with the plane of the other portions of the cleaning head arm 62.

The number of cleaning head arms 62 provided on each of the cleaning heads 50 may be up to about 30. In certain embodiments, there are between about 10 and 20 cleaning head arms 62 on each of the cleaning heads 50.

Figure 2:
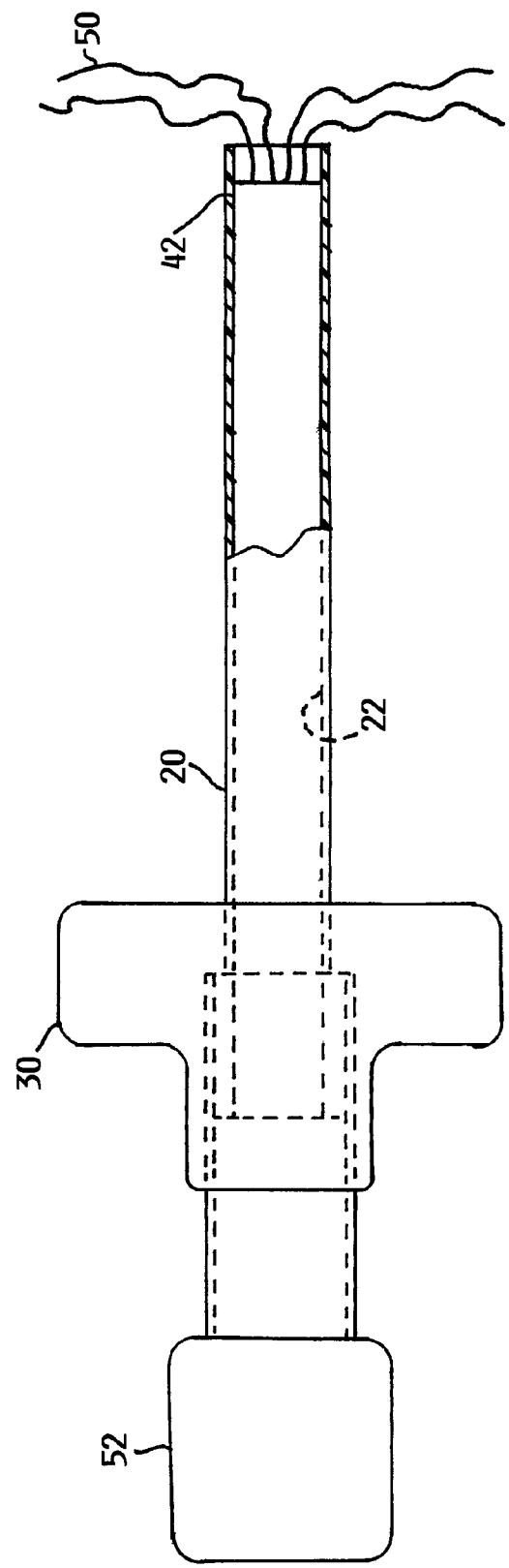
FIG. 2 is a sectional view of the radial deployment surgical tool in an extended position.

The cleaning head arms 62 may be formed with a width that is sufficiently wide so that the cleaning head arms 62 resist bending axially such as in response to rotation of the cleaning head 50. The cleaning head arms 62 may be flexible to permit bending of the cleaning head arms 62 between a retracted position within the outer shaft 22, as illustrated in FIG. 1, and an extended position, as illustrated in FIG. 2.

The cleaning head 50 may be fabricated from a relatively strong yet flexible material that provides the cleaning head 50 with the preceding characteristics. One such suitable material for fabricating the cleaning head 50 is nitinol.

In certain embodiments, the cleaning head 50 is fabricated by cutting a piece such as illustrated in FIGS. 3 and 4 from a sheet of material. The cleaning head arms 62 may then be formed into a curved configuration using a stamping process.

An advantage of using the stamping process is that the stamping process produces cleaning heads 50 with consistent shapes. Another advantage of the stamping process is that it can be automated to facilitate fabricating the cleaning head 50 in a cost-effective manner.

Figure 5:
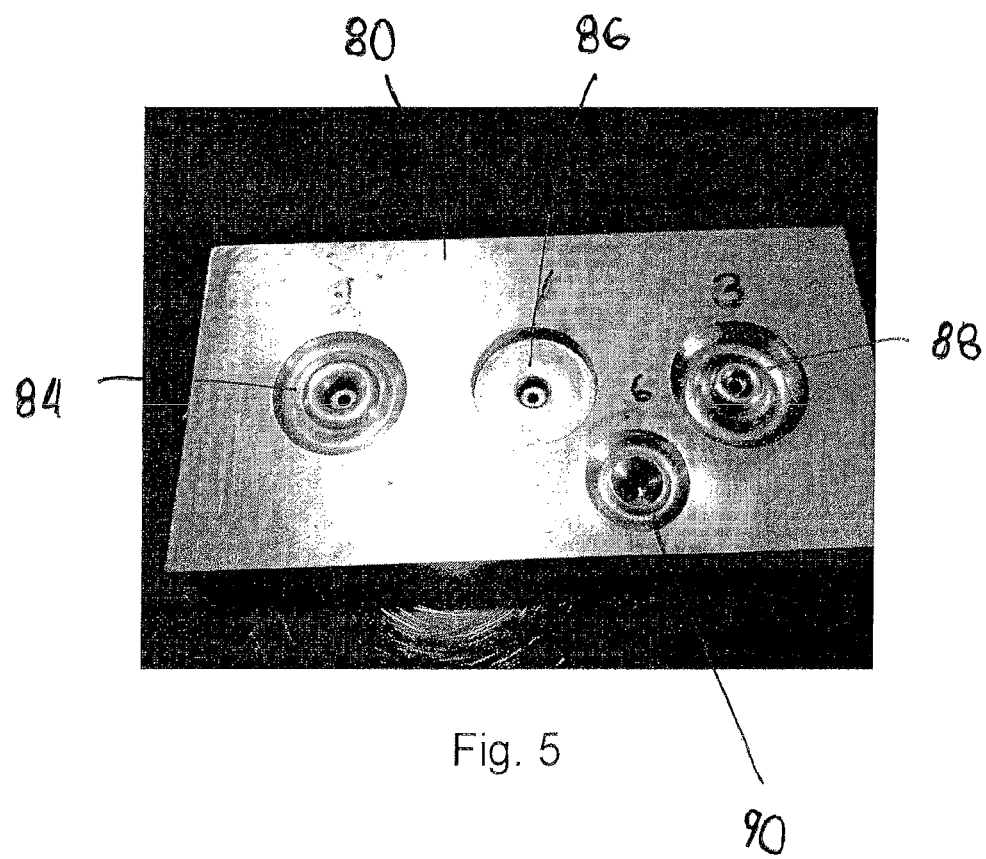
FIG. 5 is a top perspective view of a die for use in shaping the cleaning head.

At least one die 80 and at least one punch 82, such as is illustrated in FIGS. 5-7, may be used in forming the cleaning head 50 into a desired shape with the stamping process. In certain embodiments, a plurality of stamping steps may be used. As illustrated in FIG. 5, the die 80 may include a series of differently shaped recesses 84, 86, 88 and 90.

Each of the recesses 84, 86, 88, 90 may be used in conjunction with a punch having a complementary shape. FIG. 6 illustrates a punch 82 that is used in conjunction with recess 90. A person of skill in the art will appreciate that other punches may be used in conjunction with the other recesses 84, 86 and 90. FIG. 7 illustrates the punch 82 positioned at least partially in the recess 90 in the die 80.

Figure 8:
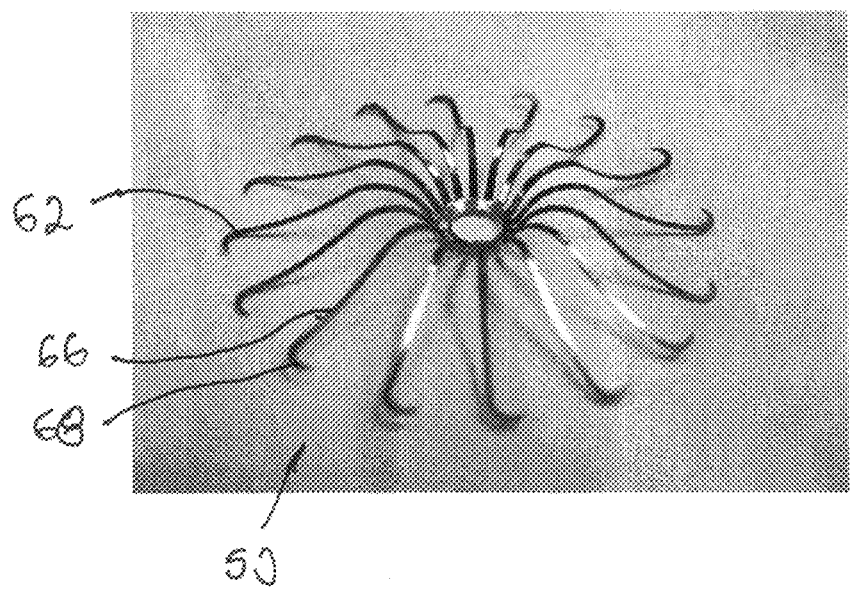
FIG. 8 is a side perspective view of the cleaning head.
Figure 9:
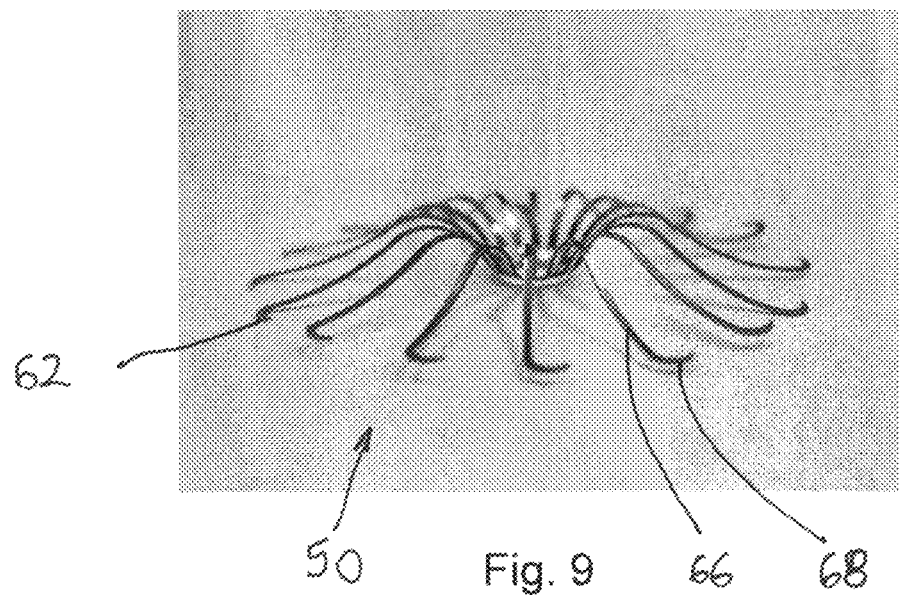
FIG. 9 is a top perspective view of the cleaning head.

After the forming process, the cleaning head 50 is shaped as is illustrated in FIGS. 8 and 9. These figures illustrate the curvature of the cleaning head arms 62. The curvature of the cleaning head arms 62 facilitates positioning the cleaning head arms 62 in a retracted position for insertion of the device as well as gradual extension of the cleaning head arms 62 within the narrow region such as is present between the sacrum and the ilium.

Figure 12:
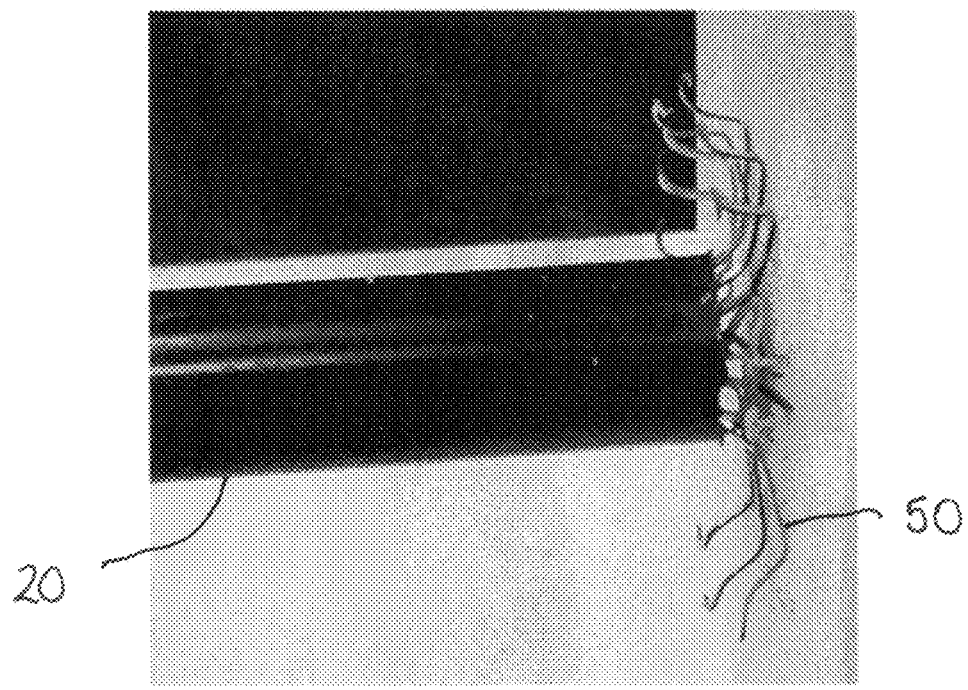
FIG. 12 is a side view of the of the surgical debris removal system with the cleaning head in an extended position.

The main portion 66 includes a first arm section 56 and a second arm section 58. The first arm section 56 is located proximate the cleaning head hub 60. The second arm section 58 is located proximate the end portion 68. When the cleaning head 50 is in the extended position, the first arm section 56 is oriented in a distal direction and the second arm section 58 is oriented in a proximal direction, as illustrated in FIGS. 8, 9 and 12.

The inner shaft 20 is rotated to cause the surgical debris to be caught in the cleaning head arms 62. In certain embodiments, the inner shaft 20 may be rotated in both a clockwise and a counterclockwise motion to catch the surgical debris.

Once the collection process is completed or the cleaning head 50 has collected near its capacity of surgical debris, the inner shaft 20 is urged towards its proximal end using the second gripping mechanism 52 until the cleaning head arms 62 are urged towards each other as the cleaning head 50 is drawn within the outer shaft 22. Once the cleaning head 50 is substantially within the outer shaft 22, the outer shaft 22 may be withdrawn from the opening in the patient.

In certain embodiments, the surgical debris removal system 10 is used in a disposable manner such that after the cleaning head 50 is used to remove surgical debris from the surgical site, the surgical debris removal system 10 is disposed of.

Alternatively, the surgical debris removal system 10 may be configured to be cleaned after use. The cleaning process could be conducted during a single surgical procedure such that the surgical debris removal system 10 is withdrawn from the patient and then processed to remove the surgical debris.

The surgical debris removal system 10 may be configured to be at least partially disposable. In such a configuration, the surgical debris removal system 10 may include a combination of some disposable components and some components that are cleaned and reused.

A variety of techniques may be used to separate the surgical debris from the cleaning head 50. An example of one suitable technique uses a compressed gas such as air. A flow of high pressure air could separate a sufficient amount of surgical debris such that the cleaning head 50 could be reinserted into the patient to remove additional surgical debris. It is also possible to use a liquid such as sterile water to separate the debris from the cleaning head 50.

Since the surgical debris removal system 10 will be reused with the same patient with this process, it is not required that all of the surgical debris be separated from the cleaning head 50. It is also not necessary that the cleaning head 50 be sterilized between uses as long as the compressed gas or liquid used to clean the cleaning head 50 is free from contaminants.

It is also possible that the surgical debris removal system 10 could be cleaned after use on a particular patient and then sterilized so that the surgical debris removal system 10 could be reused on other patients.

Each of the components of the surgical debris removal system 10 could be fabricated from a sterilizable material such as metal. To ensure that the components are cleaned and then sterilized, it is also possible for the inner shaft 20 to be separated from the outer shaft 22 during the cleaning and sterilization process.

The components of the surgical debris removal system 10 may be adapted to cause advancement or refraction of the cleaning head 50 as the handle 30 is rotated with respect to the shaft 20. In certain configurations, a right-handed thread may be used in this mechanism so that rotating the handle 30 to the right with respect to the shaft 20 will cause advancement of the cleaning head 50. Conversely, rotation of the handle 30 to the left with respect to the shaft 20 will cause retraction of the cleaning head 50.

Figure 10:
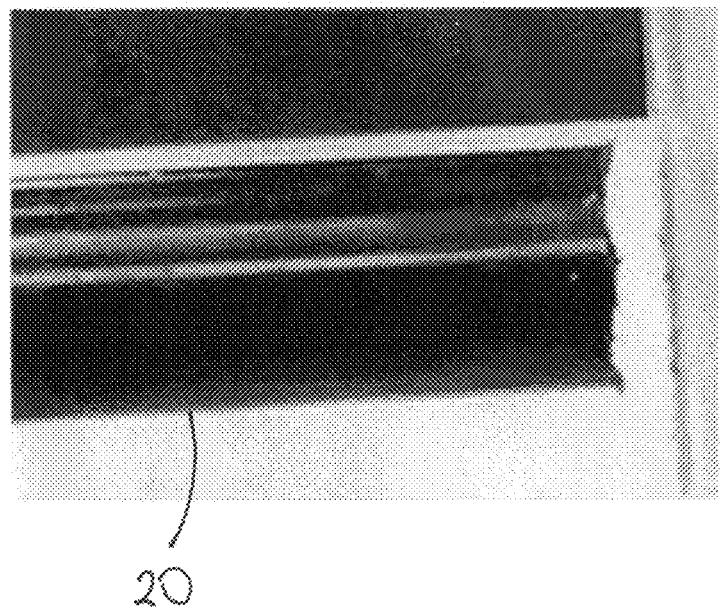
FIG. 10 is a side view of the surgical debris removal system with the cleaning head in a retracted position.
Figure 11:
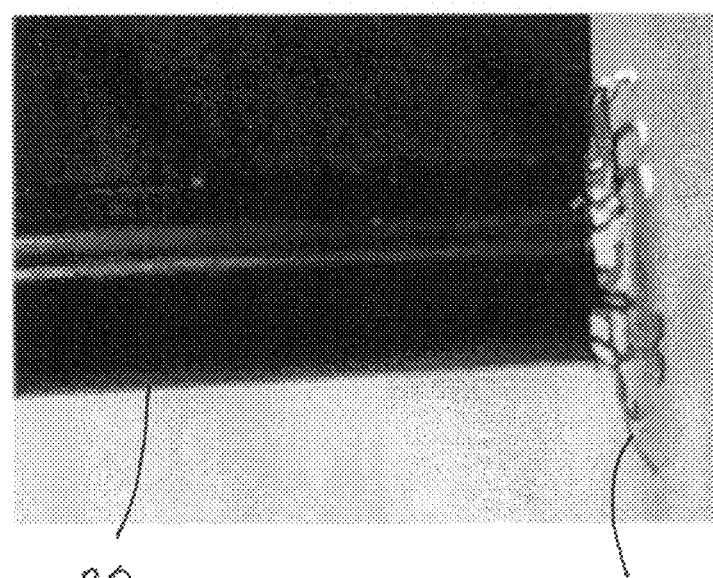
FIG. 11 is a side view of the surgical debris removal system with the cleaning head in a partially extended position

The operation of the surgical debris removal system 10 is illustrated in FIGS. 10-12. The surgical debris removal system 10 is in an initial position where the cleaning head 50 is retracted within the shaft 20, as illustrated in FIG. 10.

Rotation of the handle 30 with respect to the shaft 20 cause the cleaning head 50 to begin extending from the shaft 20, as illustrated in FIG. 11. The ends of the cleaning head arms 62 are radially deflectable so that the cleaning head arms 62 are immediately directed outward so that the cleaning head arms have a diameter that is greater than a diameter of the outer shaft 20 in response to contact with a first surface spaced the relatively small distance from the end of the shaft 20.

As the rotation of the handle 30 is continued, the ends of the cleaning head arms 62 are deflected away from the first surface, as illustrated in FIG. 12. While not shown in FIG. 12, the ends would contact a second surface that is spaced apart from the first surface. A distance between the first surface and the second surface may be less than about ½ of an inch and, in certain embodiment, may be less than about ⅛ of an inch.

The surgical debris removal system 10 may be rotated either as the cleaning head arms 62 are being extended or after the cleaning head arms 62 are extended to cause the cleaning head arms 62 to scrape over the first surface and the second surface. This movement causes the debris to be caught by the cleaning head arms 62.

After the debris collection process is completed or after the surgical debris removal system 10 has collected its capacity of debris, the cleaning head 50 is retracted into the shaft 20 so that the surgical debris removal system 10 may be removed from the patient.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of using a radial deployment surgical tool comprising:
   providing a radial deployment surgical tool comprising an outer shaft, an inner shaft and a functional head, the outer shaft having a distal end and a proximal end and the inner shaft having a distal end and a proximal end;
   operably attaching the functional head to the distal end of the inner shaft, wherein the functional head comprises a plurality of cleaning head arms, wherein each cleaning head arm comprises a main arm portion and a tip portion, wherein the main arm portion has a first arm section and a second arm section and wherein the tip portion is oriented at an angle with respect to a part of the main arm portion to which the tip portion is attached;
   inserting at least a portion of an inner shaft in the outer shaft;
   positioning the functional head in a refracted position substantially within the outer shaft;
   placing the distal end of the outer shaft in an opening in a patient;
   moving the functional head to an extended position where at least a portion of the functional head extends outside of the outer shaft so that the cleaning head arms extend to a diameter that is greater than a diameter of the outer shaft, wherein when the functional head is in the extended position, the first arm section is oriented in a distal direction and the second arm section is oriented in a proximal direction;
   rotating the inner shaft to cause the tip portions to engage tissue;
   moving the functional head to the retracted position, wherein the tip portions retain the engaged tissue in engagement as the functional head moves to the retracted position; and
   withdrawing the radial deployment surgical tool from the patient to remove the engaged tissue from the patient.

2. The method of claim 1, further comprising positioning the distal end of the outer shaft less than about ½ of an inch away from a surgical obstacle, wherein at least a portion of the functional head has a diameter that is greater than an outer diameter of the outer shaft when in the extended position.

3. The method of claim 1, further comprising attaching a stop mechanism to the outer shaft intermediate the proximal and distal ends thereof, wherein the stop mechanism limits a distance to which the outer shaft may be inserted into the opening.

4. The method of claim 3, further comprising providing a cannula that at least partially receives the outer shaft, wherein the stop mechanism engages the cannula.

5. The method of claim 1, wherein the cleaning head arms are stamped to a curved configuration.

6. The method of claim 1, wherein the functional head comprises between about 10 and 20 cleaning head arms.

7. The method of claim 1, further comprising axially rotating the functional head, wherein the cleaning head arms resist axial bending as the functional head is rotated while being bendable between a retracted position and an extended position.

8. The method of claim 1, wherein the angle is less than about 90 degrees.

9. The method of claim 1, further comprising forming each of the cleaning head arms with at least two tip portions extending therefrom.

10. The method of claim 1, further comprising attaching a plurality of the functional heads to the distal end of the inner shaft.

11. The method of claim 1, wherein the outer shaft has a bore extending therethrough and wherein the inner shaft is positionable at least partially within the bore.

12. The method of claim 1, further comprising attaching a first gripping mechanism to the outer shaft proximate the proximal end thereof.

13. The method of claim 1, further comprising attaching a second gripping mechanism to the inner shaft proximate the proximal end thereof.

* * * * *

UNITED STATES PATENT AND TRADEMARK OFFICE
CERTIFICATE OF CORRECTION

| | | |
|---|---|---|
| PATENT NO. | : 8,900,251 B2 | Page 1 of 1 |
| APPLICATION NO. | : 12/941763 | |
| DATED | : December 2, 2014 | |
| INVENTOR(S) | : Robert Assell et al. | |

It is certified that error appears in the above-identified patent and that said Letters Patent is hereby corrected as shown below:

In the Claims

In column 8, line 33, the word "refracted" should read "retracted".

Signed and Sealed this
Sixteenth Day of June, 2015

Michelle K. Lee
*Director of the United States Patent and Trademark Office*